(12) United States Patent
Kermani (10) Patent No.: US 7,010,432 B2
(45) Date of Patent: Mar. 7, 2006

(54) METHOD AND SYSTEM FOR DETERMINING THE ACCEPTABILITY OF SIGNAL DATA COLLECTED FROM A PROTHROMBIN TIME TEST STRIP

(75) Inventor: Mahyar Z. Kermani, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 245 days.

(21) Appl. No.: 10/231,929

(22) Filed: Aug. 30, 2002

(65) Prior Publication Data

US 2004/0043440 A1    Mar. 4, 2004

(51) Int. Cl.
G06F 19/00   (2006.01)
C12Q 1/56    (2006.01)
C12M 1/00    (2006.01)
G01M 1/00    (2006.01)

(52) U.S. Cl. .................. 702/19; 435/13; 435/283.1; 436/69

(58) Field of Classification Search .................. 702/19; 435/4
See application file for complete search history.

(56) References Cited

U.S. PATENT DOCUMENTS

| | | |
|---|---|---|
| 4,720,787 A | 1/1988 | Lipscomb |
| 5,526,111 A | 6/1996 | Collins et al. |
| 5,591,403 A | 1/1997 | Marcelino et al. |
| 6,046,051 A | 4/2000 | Jina |
| 6,084,660 A | 7/2000 | Shartle |
| 6,261,519 B1 | 7/2001 | Harding et al. |
| 6,673,617 B1 * | 1/2004 | Patel ............................. 436/8 |
| 6,682,933 B1 * | 1/2004 | Patel et al. ..................... 436/8 |

FOREIGN PATENT DOCUMENTS

| | | |
|---|---|---|
| EP | 0 974 840 A2 | 1/2000 |
| EP | 1 345 029 A | 9/2003 |
| EP | 1 345 030 A | 9/2003 |

\* cited by examiner

Primary Examiner—John S. Brusca (57) ABSTRACT

A method for determining the acceptability of signal data collected from a prothrombin time (PT) test strip includes collecting PT signal data from an assay area and control areas of the PT test strip. Relationships between PT signal data collected from the assay area and PT signal data collected from each of the control areas (e.g., a ratio of post-peak pseudo-slopes) are then ascertained. A determination is subsequently made, based on the relationships, as to whether the PT signal data collected from the assay area is acceptable or not for use in calculating a PT and/or an International Normalization Ratio (INR). This determination can include, for example, comparing the relationships to at least one predetermined threshold limit. A prothrombin time (PT) monitoring system includes a PT test strip and a device. The PT test strip includes an assay area and a control area. The device (e.g., a portable handheld meter) includes an optical measurement means (e.g., an LED/photo-detector pair) for measuring an optical property (e.g., absorption) of the assay area and control areas, an analog-to-digital converter module, a microprocessor module and a memory module. The optical measurement means, analog-to-digital converter module, microprocessor module and memory module are adapted to (i) collect PT signal data from the assay area and control areas; (ii) ascertain at least one relationship between PT signal data collected from the assay and control areas and (iii) determine, based on the at least one relationship, whether the PT signal data collected from the assay area is acceptable.

15 Claims, 7 Drawing Sheets

METHOD AND SYSTEM FOR DETERMINING THE ACCEPTABILITY OF SIGNAL DATA COLLECTED FROM A PROTHROMBIN TIME TEST STRIP

BACKGROUND OF THE INVENTION

1. Field of the Invention

The present invention relates, in general, to methods and systems for determining the acceptability of signal data and, in particular, to methods and systems for determining the acceptability of signal data collected from prothrombin time test strips.

2. Description of the Related Art

Typical monitoring systems for the measurement of a fluid sample characteristic include a device, such as a portable hand-held meter, and a test strip (e.g., a prothrombin time [PT] test strip) to which a fluid sample (e.g., a whole blood sample) is applied. The device and test strip are used in tandem to measure an analyte concentration (e.g., blood glucose concentration) or other characteristic (e.g., prothrombin time and/or International Normalization Ratio [INR]) of the fluid sample. The device typically measures a property or properties of the test strip (e.g., an optical reflectance, optical transmittance, optical absorption or an electrochemical property) and then employs an algorithm(s) to calculate the characteristic based on the measured property or properties.

A variety of conventional prothrombin time (PT) monitoring systems that can be employed to measure the blood-clotting time (i.e., prothrombin time) of a user's whole blood sample are known to those skilled in the art. Such conventional PT monitoring systems are described in, for example, U.S. Pat. No. 6,261,519 and U.S. Pat. No. 6,084,660, each of which is hereby fully incorporated by reference, and European Patent Application EP 0974840. These conventional PT monitoring systems are typically used by laypersons using prescription anticoagulants, such as Warfarin, to monitor their oral anticoagulation status.

Conventional PT monitoring systems can require the use of external control solutions to validate prothrombin time and/or INR test results generated by the system. Such validation is necessary to avoid erroneous results due to, for example, the use of PT test strips that have been exposed to deleterious environmental conditions (e.g., elevated temperatures and/or humidity). In this regard, PT test strips that have been exposed to extreme, although not necessarily deleterious, environmental conditions are referred to as "stressed" PT test strips.

Result validation utilizing external control solutions is based on laboratory quality control methodology, wherein results obtained with the external control solutions are assumed to mimic the performance of a user's fluid samples. However, careful attention must be paid to the matching of control solution and reagent lot numbers, and the proper control of storage and use conditions for this assumption to hold true. Unfortunately, laypersons may misunderstand or overlook the consequences of mixing lot numbers, improper storage or improper use conditions. Such misunderstandings and oversight can complicate attempts to validate the results generated by a conventional PT monitoring system. Furthermore, many users perceive the external control solutions, which require multiple preparation steps and complicated training, as difficult to employ.

Still needed in the field, therefore, are an accurate method and system for determining the acceptability of signal data obtained from a prothrombin time (PT) test strip. The method and system should be able to determine if the signal data are unacceptable due to, for example, exposure of the PT test strip to deleterious environmental conditions (e.g., elevated temperature and/or humidity). The method and system should also be capable of being integrated into a portable hand-held mater in a simple fashion.

SUMMARY OF THE INVENTION

The present invention provide methods and systems for determining the acceptability of prothrombin time signal data collected from a prothrombin time (PT) test strip. These methods and systems are relatively accurate since the determination is based on an ascertained relationship between PT signal data collected from an assay area of the PT test strip and PT signal data collected from at least one control area of the PT test strip. Such an ascertained relationship is comparative in nature and thus provides for a more accurate determination of acceptability of signal data than absolute (i.e., non-comparative) characteristics of the PT signal data.

Furthermore, since embodiments of the present invention employ computationally efficient techniques to ascertain the relationship, the methods and systems can be easily and simply deployed using, or integrated in, a portable hand-held meter. In addition, the methods and systems according to embodiments of the present invention do not require the use of external standard solutions.

A method for determining the acceptability of signal data collected from a prothrombin time (PT) test strip according to an exemplary embodiment of the present invention includes collecting prothrombin time (PT) signal data from an assay area and at least one control area of a prothrombin time test strip. The PT test strip employed in methods according to the exemplary embodiment of the present invention can be any suitable PT test strip known to one skilled in the art that includes both an assay area and at least one control area. Suitable PT test strips encompass those with an assay area, a first control area and a second control area, such as those described in U.S. Pat. No. 6,261,519, U.S. Pat. No. 6,084,660 and U.S. patent application Ser. No. 10/100,254 (filed on Mar. 14, 2002), each of which is hereby fully incorporated by reference.

Following collection of the above-mentioned PT signal data, at least one relationship between PT signal data collected from the assay area and PT signal data collected from the at least one control area is ascertained. The relationship which is ascertained is comparative in nature and, therefore, a more accurate determinate of the acceptability of the PT signal data than an absolute characteristic of the PT signal data. Suitable relationships include, but are not limited to, ratio-metric relationships such as the ratio of post-peak pseudo-slopes of PT signal data collected from the assay area and the at least one control area, the ratio of PT signal data peak widths collected from the assay area and the at least one control area, and the ratio of the areas underneath PT signal data collected from the assay area and the at least one control area.

Next, a determination is made, based on the relationship, as to whether the PT signal data collected from the assay area is acceptable or not acceptable. Acceptable PT signal data can then be employed, for example, in calculating a prothrombin time and/or an INR. The determination can include, for example, comparing the relationship to at least one predetermined threshold limit.

Another embodiment of the present invention is a PT monitoring system that includes a PT test strip and a device. The PT test strip includes an assay area and at least one control area. The device (e.g., a portable hand-held meter) includes means for measuring a property (e.g., optical reflectance) of the assay area and of the at least one control area. The device also includes an analog-to-digital converter module, a microprocessor module and a memory module. In this embodiment of the present invention, the property measurement means, analog-to-digital converter module, microprocessor module and memory module are adapted to (i) collect PT signal data from the assay area and the at least one control area; (ii) ascertain at least one relationship between PT signal data collected from the assay area and PT signal data collected from the at least one control area; and (iii) determine, based on the at least one relationship, whether the PT signal data collected from the assay area is acceptable.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF PREFERRED EMBODIMENTS

To be consistent throughout the present specification and for clear understanding of the present invention, the following definition is hereby provided for a term used therein:

The term "prothrombin time (PT) signal data" refers to data collected from a PT test strip by a device for purposes of calculating a prothrombin time and/or an INR of a fluid sample applied to the PT test strip. Such PT signal data include not only raw (e.g., as-observed) signal data, but also signal data that are the results of manipulation, transformation and/or conversion of raw signal data by means of hardware and/or software. Such PT signal data can include, for example, signal amplitude data, e.g., electrical current, electrical voltage or ADC count data, as a function of time.

Figure 1:
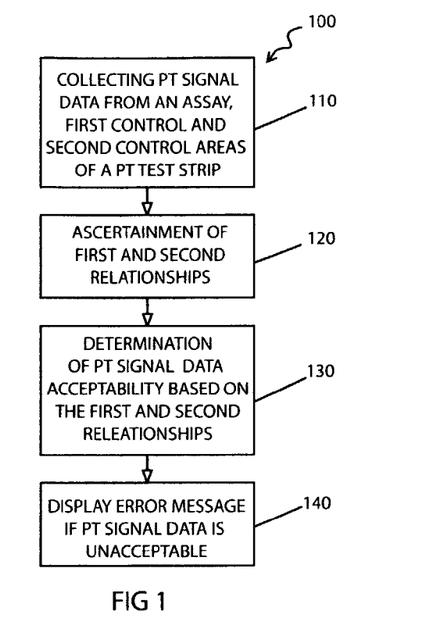
FIG. 1 is a is a flow diagram illustrating a sequence of steps in a process according to an exemplary embodiment of the present invention.
Figure 2:
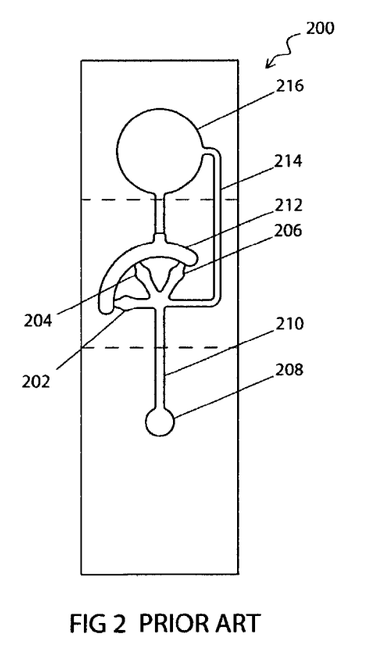
FIG. 2 is a simplified depiction of a prothrombin time test strip that can be employed in conjunction with the exemplary process of FIG. 1.

FIG. 1 is a flow chart illustrating a sequence of steps in a process 100 for determining the acceptability of prothrombin time signal data collected from a prothrombin time test strip according to one exemplary embodiment of the present invention. For the purpose of explanation only, process 100 will be described in terms of PT signal data collected from a PT test strip 200 (illustrated in FIG. 2) that includes an assay area 202, a first control area 204 and a second control area 206. As depicted in FIG. 2, PT test strip 200 also includes a sample port 208, channel 210, stop junction 212, bypass channel 214 and bladder 216.

Assay area 202 contains a reagent (e.g., a thromboplastin reagent) that is employed in the measurement of PT and/or INR. First control area 204 contains reagents with sufficient coagulation factors to counteract any effects of an anticoagulant (e.g., Warfarin) present in a whole blood sample applied to sample port 208 of PT test strip 200. Second control area 206 contains a different composition and quantity of coagulation factors such that a partial normalization of the anticoagulant present in the whole blood sample can be achieved. Details related to the structure and operation of PT test strip 200 and the composition of reagents employed in the assay area, first control area and second control area are described in U.S. Pat. No. 5,230, 866, U.S. Pat. No. 6,261,519, U.S. Pat. No. 6,084,660 and U.S. patent application Ser. No. 10/100,254 (filed on Mar. 14, 2002), each of which is hereby fully incorporated by reference.

Process 100 includes first collecting prothrombin time (PT) signal data from an assay area, a first control area and a second control area of PT test strip 200, as set forth in step 110 of FIG. 1. The PT signal data collected from the assay area are referred to as A, while the PT signal data collected from the first and second control areas are referred to as C1 and C2, respectively. One skilled in the art will recognize that processes according to the present invention can be adapted to PT test strips with one or more control areas.

In process 100, the collected PT signal data represent sequential measurements of light scattering and/or absorption through portions of a whole blood sample that have been drawn into the assay area 202, first control area 204 and second control area 206 of the PT test strip 200 through channel 210. These sequential measurements are made at a predetermined time interval (i.e., index) of, for example, every 0.15 seconds. A device, such as a portable hand-held meter with an optical measurement means (e.g., an LED/photo-detector pair), can be used to measure the light (optical) scattering and/or absorption and to collect the PT signal data. However, processes according to the present invention are not limited to the measurement of light scattering and/or absorption. Once apprised of the present disclosure, one skilled in the art will recognize that the process can be adapted to include PT signal data that represent a variety of properties of the assay area, and first and second control areas, including electrical, magnetic, fluidic and optical properties.

Figure 3:
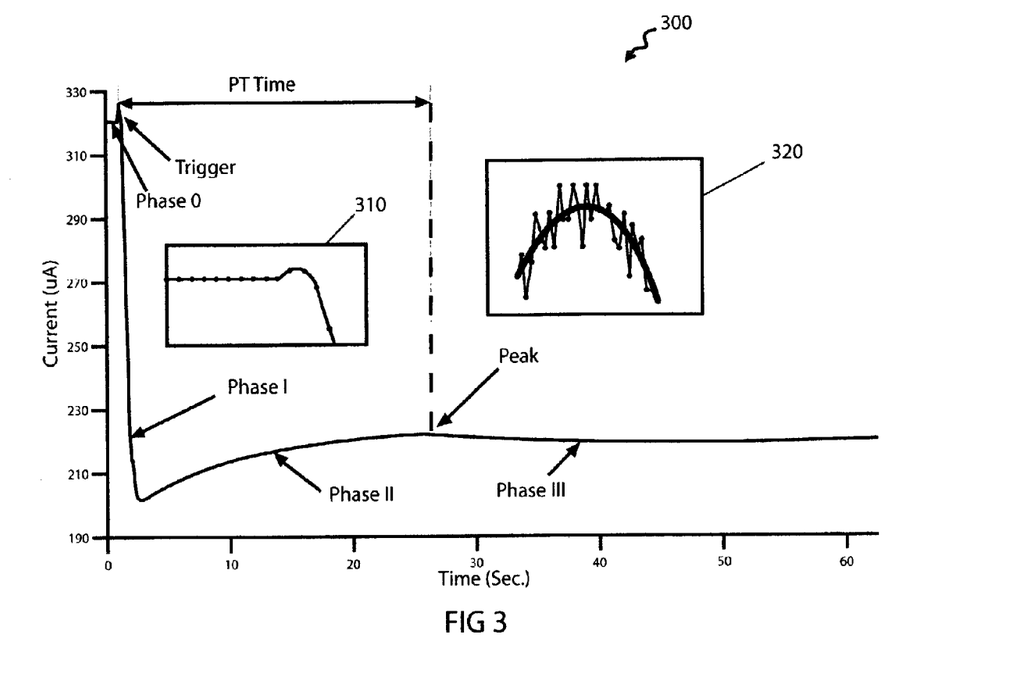
FIG. 3 is a graph depicting a PT signal data, including expanded views of the trigger and peak point areas, as can be collected in a process according to the present invention.

FIG. 3 is a graph 300 depicting PT signal data, including an expanded view of a trigger area 310 and an expanded view of a peak point area 320, as can be collected in a process according to an exemplary embodiment of the present invention. The PT signal data of FIG. 3 made up of sequential current versus time data points, as illustrated in expanded views 310 and 320.

The PT signal data have four major phases. The initial phase (i.e., Phase 0), also referred to as a pre-trigger point phase, corresponds to a time period when an assay or control area of the PT test strip does not contain any fluid sample. During Phase 0, the PT signal data are of a constant value and this constant value can be considered a baseline for comparing other portions of the PT signal data. In a second phase (i.e., Phase I), a rapid drop in the amplitude of the values of the PT signal data occurs. This rapid drop is caused by the filling of the assay or control area of the PT test strip with fluid sample. The transition point from Phase 0 to Phase I is referred to as the "trigger point."

After the assay or control area is full and the fluid sample stops flowing in the PT test strip, the amplitude of the PT signal data will rise (see Phase II of FIG. 3) and thereafter start to decline (see Phase III of FIG. 3). The rise and fall during phase II and phase III create a peak point in the PT signal data. The prothrombin time is defined as the time elapsed between the trigger point and the peak point. This elapsed time is labeled "PT time" in FIG. 3.

Figure 4:
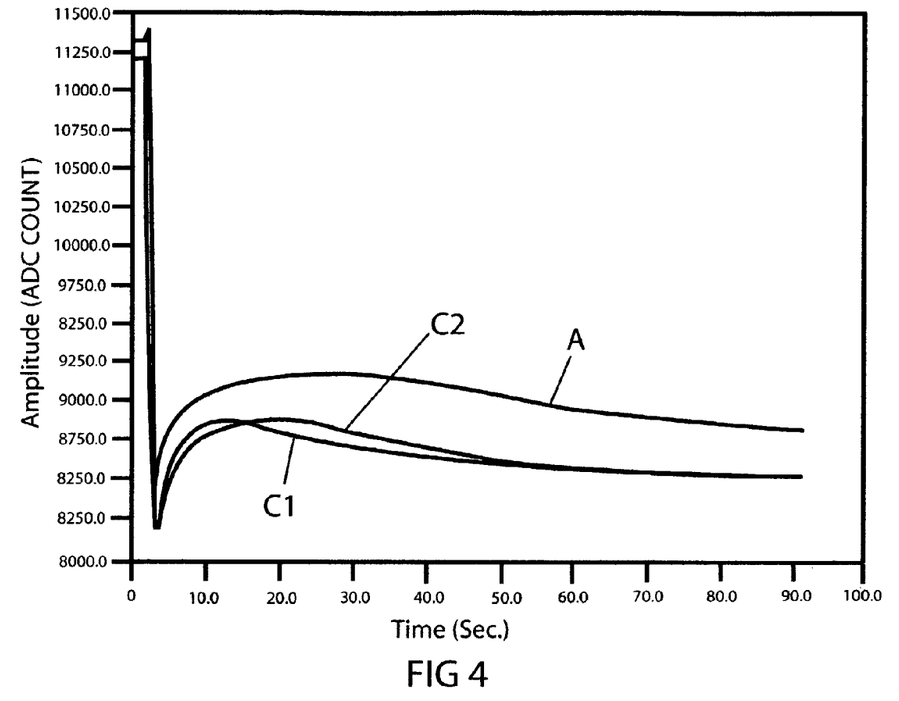
FIG. 4 is a graph depicting PT signal data from an assay area, a first control area and a second control area as can be collected in a process according to an exemplary embodiment of the present invention.
Figure 5:
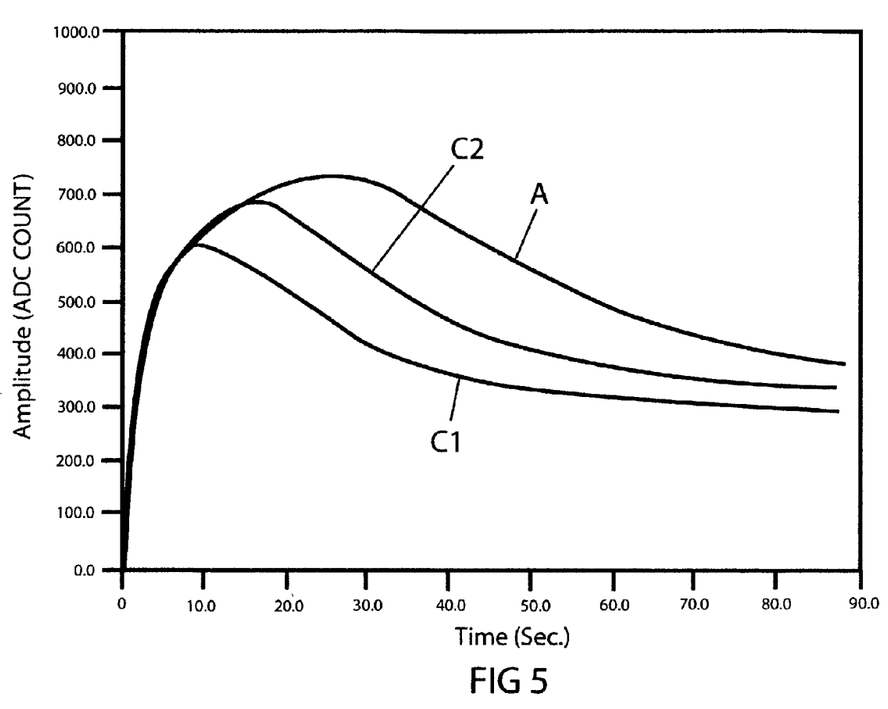
FIG. 5 is a graph depicting the PT signal data of FIG. 4 after truncation and alignment to their respective minimum points.
Figure 6:
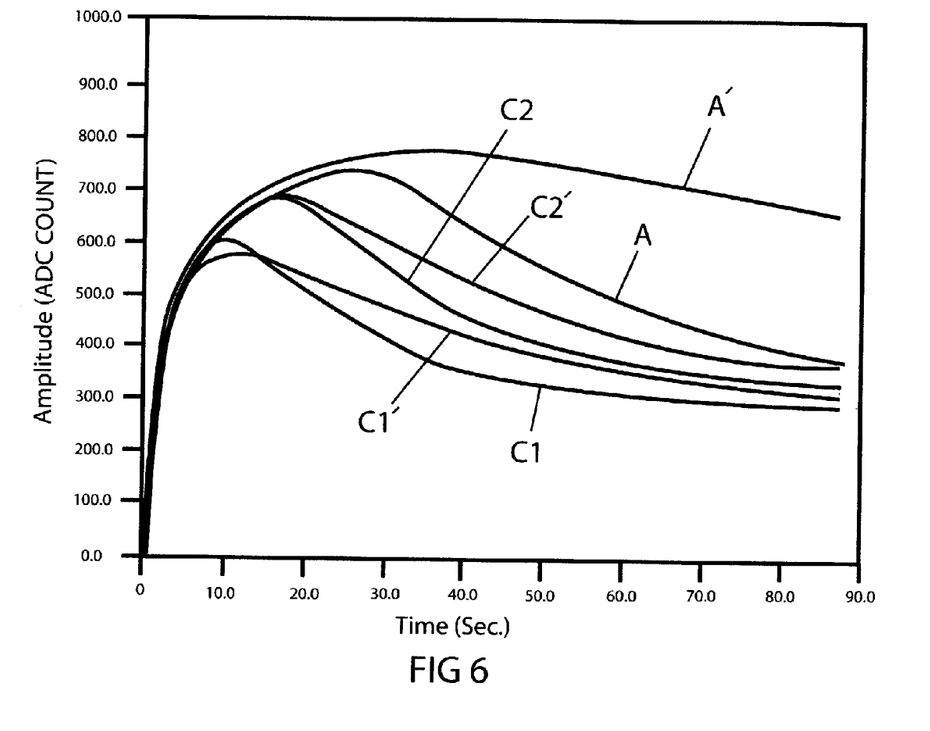
FIG. 6 is a graph depicting the PT signal data of FIG. 5 along with PT signal data collected from a stressed PT test strip.
Figure 7:
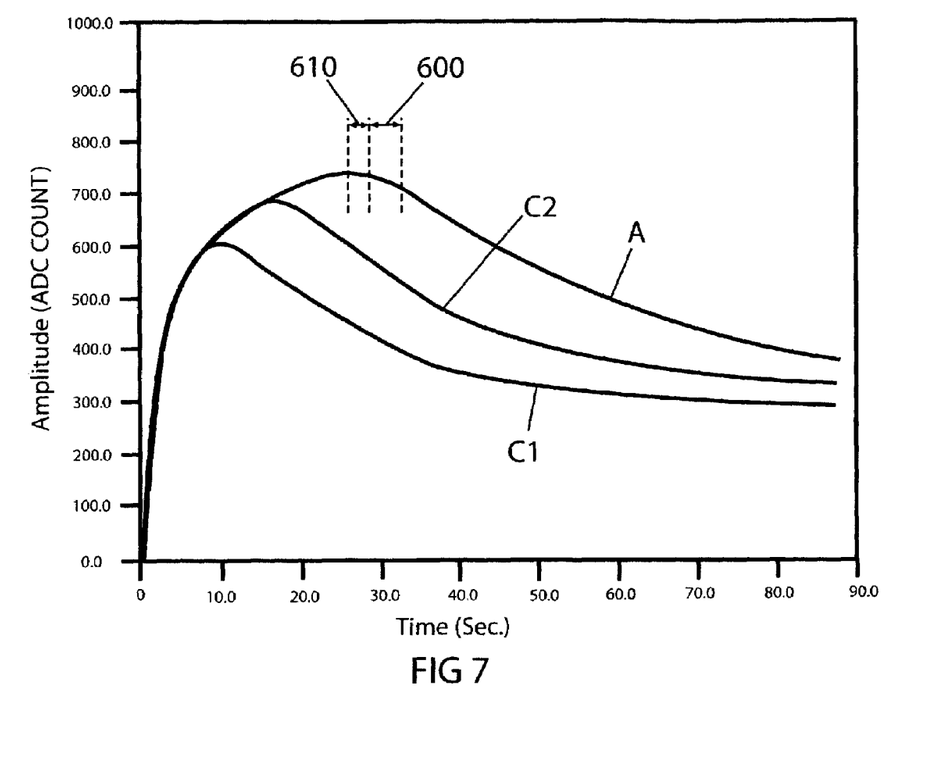
FIG. 7 is a graph depicting the PT signal data of FIG. 5 and a post-peak window of the PT signal data collected from an assay area.

FIG. 4 is a graph depicting PT signal data from an assay area (A), a first control area (C1) and a second control area (C2) of a standard (reference) PT test strip, as can also be collected in a process according to an exemplary embodiment of the present invention. Standard PT test strips are PT test strips that have not been exposed to deleterious conditions and can serve as a reference. FIG. 5 is a graph depicting the PT signal data of FIG. 4 after truncation and alignment to their respective minimum points. Truncation and alignment to the minimum points provide for an easier visualization of the relationship between the various PT signal data. FIG. 6 is a graph depicting the PT signal data of FIG. 5 along with PT signal data collected from a stressed PT test strip. The PT signal data collected from the assay area, first control area and second control area of the stressed PT test strip are labeled A', C1' and C2' respectively.

FIG. 6 serves to visually illustrate that the relationship between the PT signal data collected from the assay area and first and second control areas of the stressed PT test strip is different from the relationship between PT signal data collected from the standard (reference) PT test strip. For example, the post-peak slopes for A, C1 and C2 appear visibly parallel, while the post-peak slopes for A', C1' and C2' do not appear visibly parallel. Such differences are employed in the present invention to determine the acceptability of PT signal data.

Next, a first relationship and a second relationship are ascertained, as set forth in step 120. The first relationship is established between PT signal data collected from the assay area and those collected from the first area, while the second relationship is established between PT signal data collected from the assay area and those collected from the second control area. In process 100, the first relationship is the ratio of a post-peak pseudo-slope of A and that of C1, while the second relationship is the ratio of a post-peak pseudo-slope of A and that of C2. However, the relationships ascertained in processes according to the present invention are not limited to the aforementioned post-peak pseudo-slopes. Once apprised of the present disclosure, one of ordinary skill in the art can ascertain other suitable relationships including, but not limited to, ratios of peak widths and ratios of areas underneath the PT signals.

The first and second relationships of process 100 can be ascertained using, for example, the following technique. First, the peak points for C1, C2 and A are resolved. These peak points are referred to as C1(p1), C2(p2) and A(pa), where p1, p2 and pa are the peak indices for C1, C2 and A, respectively. In this regard, one skilled in the art will recognize that "indices" (such as the peak indices) are employed to represent points on a time axis of C1, C2 and A. The peak points can be resolved using any methods known to one skilled in the art including, but not limited to, taking the 1st derivative of C1, C2 and A and resolving where these first derivatives cross zero.

Next, a portion of each of the C1, C2 and A signals located after their respective peak points (i.e., after C1(p1), C2(p2) and A(pa)) is selected. Each of these portions is referred to as a "post-peak window" and has a window width "w." The terms C1W, C2W and AW are used to refer to the post-peak windows of the C1, C2 and A, respectively. FIG. 6 is the PT signal data graph of FIG. 4 identifying a post-peak window 600 of the A PT signal data and the starting index sa (610) of the A PT signal data.

In general, the PT signal data within the post-peak windows can be represented by the following three equations:

$$C1W = \{C1(p1+s1), C1(p1+s1+1), \ldots, C2(p2+s2+w2-1)\} \quad (1)$$

$$C2W = \{C2(p2+s2), C2(p2+s+1), \ldots, C2(p2+s2+w2-1)\} \quad (2)$$

$$AW = \{A(pa+sa), A(pa+sa+1), \ldots, A(pa+sa+wa-1)\} \quad (3)$$

where:
w1 is the width of C1W;
w2 is the width of C2W;
wa is the width of AW;
s1 is the starting index of the window C1W;
s2 is the starting index of window C2W; and
sa is the starting index of window AW.

The widths (w1, w2 and wa) and starting indices (s1, s2 and sa) can be predetermined based on an analysis of standard PT test strips and PT test strips that have been exposed to deleterious environmental conditions. The values of s1, s2 and sa can be any suitable value, for example, values in the range of 5 to 40. In process 100, w1, w2 and wa are fixed at a value 31. Alternatively, the starting indices s1, s2 and sa can be adaptively determined based on the peak points and trigger points of C1, C2 and A using the following sets equations:

$$s1 = \begin{cases} k1*(p1-t1-k2) & \text{if } s1 \le k3 \\ k3 & \text{otherwise} \end{cases} \quad (4)$$

$$s2 = \begin{cases} k1*(p2-t2-k2) & \text{if } s2 \le k3 \\ k3 & \text{otherwise} \end{cases} \quad (5)$$

$$sa = \begin{cases} k1*(pa-ta-k2) & \text{if } sa \le k3 \\ k3 & \text{otherwise} \end{cases} \quad (6)$$

where:
k1, k2 and k3 are predetermined constants;
t1 is the trigger point index of C1;
t2 is the trigger point index of C2; and
ta is the trigger point index of A.

The value of k1, k2 and k3 can be any value that provides for a suitable adaptive calculation of s1, s2 and sa. Typical values are a k1 of 0.15; a k3 of 40; and a k2 of zero. Since k2, in effect, serves to determine a minimum time at which an adaptive window is started, when k2 is set equal to zero there is essentially no predetermined minimum time limit for the start of an adaptive window. If desired, the window widths can also be adaptively determined. However, to implement the processes according to the present invention using a limited microprocessor module, it is beneficial to use fixed window widths and, thereby, minimize the required computational resources. Furthermore, the set of equations for adaptively determining the starting indices can be based on other characteristics of the signal data, such as minimum points of the signal data. However, use of the trigger points (as in equations 4, 5 and 6 above) has the benefit of being relatively insensitive to noise in the signal data.

The use of the adaptive algorithm described above reduces the dependency of post-peak pseudo-slope on INR since it adjusts the location of the post-peak window based on the peak points of the collected PT signal data (which differs with INR).

After selecting the post-peak windows (i.e., C1W, C2W and AW), the pseudo-slope of the portions of the PT signal data within each of the post-peak windows is calculated. These pseudo-slopes can be calculated, using, for example, a least squares line fitted to the PT signal data within C1W, C2W and AW as follows:

$$PS1 = \sum_{i=1}^{w1} \left[ \left( i - \frac{(w1+1)}{2} \right) C1W(i) \right] \quad (7)$$

$$PS2 = \sum_{i=1}^{w2} \left[ \left( i - \frac{(w2+1)}{2} \right) C2W(i) \right] \quad (8)$$

$$PSa = \sum_{i=1}^{wa} \left[ \left( i - \frac{(wa+1)}{2} \right) AW(i) \right] \quad (9)$$

where:
i represents indices of the PT signal data within the post-peak window;
PS1 is the post-peak pseudo-slope of PT signal data within C1W;
PS2 is the post-peak pseudo-slope of PT signal data within C2W; and
PSa is the post-peak pseudo-slope of PT signal data within AW.

Equations (7) through (9) are derived from a normal regression slope equation that has been simplified under the assumption that all of the PT signal data are collected using a uniform sampling rate. Under this assumption, constant denominators in the normal regression slope equations are eliminated to save computational time and resources.

Once apprised of the equations for calculating post-peak pseudo-slope above, one skilled in the art will recognize that when w1, w2 and wa are odd numbers, the "weights" (i.e., the term represented by one half of the sum of the window width+1) for C1W, C2W and AW in equations (7) through (9) are integers and that, therefore, these calculations can be done in integer format to further reduce processing time. In addition, a similar advantage can be achieved by multiplying the weights by a factor of two.

Next, the first relationship (i.e., ratio of the post-peak pseudo-slopes calculated for A and C1) and the second relationship (i.e., the ratio of the post-peak pseudo-slopes calculated for A and C2) are calculated. The equations representing these relationships can be written as:

$$\text{First relationship} = f1 = \frac{PSa}{PS1} \quad (10)$$

$$\text{First relationship} = f2 = \frac{PSa}{PS2} \quad (11)$$

Ratio-metric relationships, such as the post-peak pseudo-slopes described above, are especially beneficial in determining the acceptability of PT signal data since they are comparative in nature and, therefore, relatively independent of blood type, PT test strip lot and INR. Once apprised of the present disclosure, one skilled in the art will recognize that other conventional mathematical, numerical or modeling techniques can be used to ascertain the first and/or second relationships and that the present invention is not limited to the equations detailed above.

After having ascertained the first and second relationships, a determination is made, based on these relationships, as to the acceptability of the PT signal data collected from the assay area, as set forth in step 130 of FIG. 1. This determination can be accomplished, for example, by comparing the post-peak pseudo-slopes calculated from equations (10) and (11) above to predetermined threshold limits (e.g., predetermined acceptance specifications).

Alternatively, the determination of step 130 can be made in the following manner. First, steps 110 and 120 are conducted on a plurality of standard PT test strips (i.e., PT test strips which have not been exposed to deleterious conditions, also referred to as non-stressed PT test strips). The result is a set of post-peak pseudo-slopes for the plurality of standard PT test strips. This set is then used to calculate the mean and covariance matrix of the standard PT test strips. Any measurement in the f1 and f2 feature space is then normalized according to the following equations:

$$f_n = \sum\nolimits^{-\frac{1}{2}} * (f - M); f_n = \begin{pmatrix} fn1 \\ fn2 \end{pmatrix}; f = \begin{pmatrix} f1 \\ f2 \end{pmatrix} \quad (12)$$

where:
$f_n$ is the normalized feature space of f.
M is the mean vector of the non-stressed PT test strips; and
$\Sigma$ is the covariance matrix of the non-stressed PT test strips.

In this alternative process, step 130 would then involve a determination of whether $$fn1 \leq k \text{ OR } fn2 \leq k \quad (13)$$

where k is an error detection threshold. The error detection threshold is selected based on maximum allowable false positives for lots of non-stressed PT test strips. To limit the percentage of false positives in the standard non-stressed PT test strips to 0.7%, the k value was determined to be 2.45 using a one-tailed normal distribution.

By transforming to an alternative space (as described above with respect to equation set (12)), the interdependency (i.e., correlation) of the first and second relationships can eliminated, thereby providing for transformed first and second relationships to be compared to independent predetermined threshold limits.

Next, as set forth in step 140, an error message is displayed when a determination has been made in step 130 that the PT signal data from the PT test strip is unacceptable. If desired, different error messages can be displayed depending on whether the first and/or second relationship was the basis for determining that the PT signal data was unacceptable.

It should be noted that the equations described above are computationally efficient and can be implemented in devices (e.g., portable hand-held meters) with limited microprocessor capability. Studies on standard PT test strips and stressed PT test strips (PT test strips that had been exposed to deleterious environmental conditions, i.e., 38° C./85% R.H., for up to 48 hours) indicated that process 100 (including the use of equations [1] through [13] above) produces a very low rate of false negatives for stressed PT test strips and does not produce an unacceptable rate of false positives for the standard PT test strips.

Figure 8:
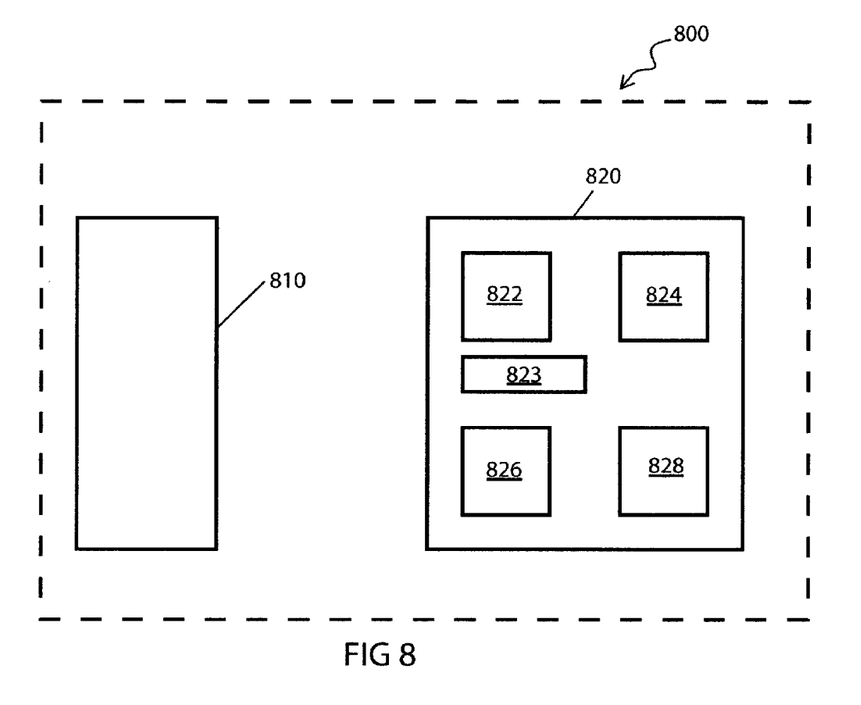
FIG. 8 is a simplified block diagram of a PT monitoring system according to an exemplary embodiment of the present invention.

FIG. 8 is a simplified block diagram depicting a prothrombin time (PT) monitoring system 800 (within the dashed lines) according to one exemplary embodiment of the present invention. PT monitoring system 800 includes a PT test strip 810 and a device 820. PT test strip 810 includes an assay area and at least one control area (neither of which are shown in FIG. 8). PT test strip 810 can include, for example, an assay area, a first control area and a second control area. Therefore, PT test strip 200 of FIG. 2 serves as an example of a PT test strip that can be included in PT monitoring system 800.

Device 820 includes an optical measurement means 822 (e.g., an LED/photo-detector pair), an analog-to-digital converter module 823, a microprocessor module 824, a memory module 826 and a display module 828. Modules 823, 824 and 826 can be implemented using available commercial parts or can be implemented as a part of an ASIC (Application Specific Integrated Circuit). Device 820 can take the form, for example, of a portable hand-held meter.

Optical measurement means 822 is adapted for measuring an optical property of the assay area and the at least one control area of PT test strip 810. Analog-to-digital converter module 823 is configured for converting an analog output of the optical measurement means 822 to a digital signal. Microprocessor module 824, memory module 826 and display module 828 can take any suitable form known to one skilled in the art.

In PT monitoring system 800, optical measurement means 822, analog-to-digital converter module 823, microprocessor module 824 and memory module 826 are adapted to:
(i) collect PT signal data from the assay area, as well as from the at least one control area of the PT test strip;
(ii) ascertain at least one relationship between PT signal data collected from the assay area and those collected from the at least one control area; and
(iii) determine, based on the at least one relationship, whether the PT signal data collected from the assay area is acceptable.

In essence, device 820 is adapted to perform the inventive processes described above, including process 100. Once apprised of the present disclosure, one of ordinary skill in the art can implement such an adaptation of optical measurement means 822, analog-to-digital converter module 823, microprocessor module 824 and memory module 826 through conventional use of software, firmware and/or hardware. Furthermore, the microprocessor module, memory module and display can be adapted to display an error message to a user when a determination has been made that the PT signal data collected from the assay area is unacceptable.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the acceptability of signal data collected from a prothrombin time (PT) test strip, the method comprising:
   collecting prothrombin time (PT) signal data from an assay area of a PT test strip and PT signal data from at least one control area of the PT test strip;
   ascertaining at least one relationship between PT signal data collected from the assay area and PT signal data collected from the at least one control area; and
   determining, based on the at least one relationship, whether the PT signal data collected from the assay area is acceptable by comparing the at least one relationship to at least one predetermined threshold limit, wherein the at least one relationship is selected from the relationship group consisting of a ratio of a post-peak pseudo-slope of PT signal data from the assay area and a post-peak pseudo-slope of PT signal data from at least one control area, a ratio of a peak width of PT signal data from the assay area and peak width of PT signal data from the at least one control area, and a ratio of an area underneath the PT signal data from the assay area and the area underneath the PT signal data from the at least one control area; and wherein the predetermined threshold limit is based on PT signal data collected from standard reference PT test strips.

2. The method of claim 1, wherein the ascertaining step ascertains the at least one relationship using a technique that includes:
   resolving a peak point of the PT signal data collected from the assay area and a peak point of the PT signal data collected from the at least one control area;
   selecting a first post-peak window of the PT signal data collected from the assay area and a second post-peak window of the PT signal data collected from the at least one control area;
   calculating the post-peak pseudo-slopes for the first and second post-peak window; and
   calculating a ratio of the post-peak pseudo-slope of the first window and the post-peak pseudo-slope of the second window, thereby ascertaining the ratio as the at least one relationship.

3. The method of claim 2, wherein the post-peak psdueo-slopes for the first and second post-peak windows are calculated using a least-squares fitted-line technique.

4. The method of claim 2, wherein the selecting step selects the first and second post-peak windows using predetermined fixed window widths and predetermined fixed window start indices.

5. The method of claim 1, wherein the determining step includes normalizing the relationship and comparing the normalized relationship to a predetermined threshold limit.

6. The method of claim 1, further including the step of:
   displaying an error message to a user when a determination is made during the determining step, by comparing the at least one relationship to at least one predetermined threshold limit, that the PT signal data collected from the assay area is unacceptable.

7. The method of claim 1, wherein:
   the collecting step includes collecting PT signal data from the assay area, a first control area and a second control area of the PT test strip;
   the ascertaining step includes ascertaining a first relationship between PT signal data collected from the assay area and PT signal data collected from the first control area and ascertaining a second relationship between PT signal data collected from the assay area and PT signal data collected from the second control area, and
   the determining step includes determining whether the PT signal data collected from the assay area is acceptable based on comparing the first relationship and the second relationship to predetermined threshold limits.

8. The method of claim 7, further including the step of:
   displaying an error message to a user when a determination is made during the determining step that the PT signal data collected from the assay area is unacceptable based on the comparing of the first relationship and the second relationship to the predetermined threshold limits.

9. The method of claim 8, wherein the displaying step displays a first error message when a determination is made during the determining step that the PT signal data collected from the assay area is unacceptable based on the first relationship, displays a second error message when a determination is made during the determining step that the PT signal data collected from the assay area is unacceptable based on the second relationship, and displays a third error message when a determination is made during the determining step that the PT signal data collected from the assay area is unacceptable based on both the first and second relationships.

10. A method for determining the acceptability of signal data collected from a prothrombin time (PT) test strip, the method comprising:
    collecting prothrombin time (PT) signal data from an assay area of a PT test strip, PT signal data from a first control area of the PT test strip and OT signal data from a second control area of the PT test strip;
    ascertaining a first relationship between PT signal data collected from the assay area and PT signal data collected from the first control area and ascertaining a second relationship between PT signal data collected from the assay area and PT signal data collected from the second control area; and
    determining, based on the first and second relationships, whether the PT signal data collected from the assay area is acceptable for use in accurately determining prothrombin time by comparing the first relationship and the second relationship to predetermined threshold limits,
wherein the first relationship is a ratio of a post-peak pseudo-slope of PT signal data from the assay area and a post-peak pseudo-slope of PT signal data from the first control area and the second relationship is a ratio of post-peak pseudo-slope of PT signal data from the assay area and a post-peak pseudo-slope of PT signal data from the second control area; and
wherein the predetermined threshold limits are based on PT signal data collected from standard reference PT test strips.

11. A prothrombin time (PT) monitoring system comprising:
    a prothrombin time (PT) test strip that includes:
        an assay area; and
        at least one control area; and
    a device that includes:
        an optical measurement means for measuring an optical property of the assay area and the at least one control area;
        an analog-to-digital converter module;
        a microprocessor module; and
        a memory module,
    wherein the optical measurement means, analog-to-digital converter module, microprocessor module and memory module are adapted to:
        collect prothrombin time (PT) signal data from the assay area and PT signal data from the at least one control area;
        ascertain at least one relationship between PT signal data collected from the assay area and PT signal data collected from the at least one control area; and
        determine, based on the at least one relationship, whether the PT signal data collected from the assay area is acceptable by comparing the first relationship to a predetermined threshold limit,
    wherein the at least one relationship is selected from the relationship group consisting of a ratio of a post-peak pseudo-slope of PT signal data from the assay area and a post-peak pseudo-slope of PT signal data from at least one control area, a ratio of a peak width of PT signal data from the assay area and peak width of PT signal data from the at least one control area, and a ratio of an area underneath the PT signal data from the assay area and the area underneath the PT signal data from the at least one control area; and
    wherein the predetermined threshold limit is based on PT signal data collected from standard reference PT test strips.

12. The PT monitoring system of claim 11, wherein the device further includes a display module and wherein the microprocessor module, memory module and display module are adapted to display an error message to a user when a determination has been made that the PT signal data collected from the assay area is unacceptable by comparing the first relationship and the second relationship to predetermined threshold limits.

13. The PT monitoring system of claim 11, wherein the PT test strip includes the assay area, a first control area and a second control area and wherein the optical measurement means, analog-to-digital converter module, microprocessor module and memory module are adapted to:
    collect PT signal data from the assay area, the first control area and the second control area;
    ascertain a first relationship between PT signal data collected form the assay area and PT signal data collected from the first control area and a second relationship between PT signal data collected from the assay area and PT signal data collected from the second control area; and
    determine, based on the first and second relationships, whether the PT signal data collected from the assay area is acceptable by comparing the first relationship and the second relationship to predetermined threshold limits,
    wherein the first relationship is a ratio of a post-peak pseudo-slope of PT signal data from the assay area and a post-peak pseudo-slope of PT signal data from the first control area and the second relationship is a ratio of post-peak pseudo-slope of PT signal data from the assay area and a post-peak pseudo-slope of PT signal data from the second control area.

14. The PT monitoring system of claim 11, wherein the device is a portable hand-held meter.

15. The PT monitoring system of claim 11, wherein the optical measurement means is an LED/photo-detector pair.

* * * * *